US008527208B2

(12) United States Patent
Prud'homme et al.

(10) Patent No.: US 8,527,208 B2
(45) Date of Patent: Sep. 3, 2013

(54) PRANDIAL BLOOD GLUCOSE EXCURSION OPTIMIZATION METHOD VIA COMPUTATION OF TIME-VARYING OPTIMAL INSULIN PROFILES AND SYSTEM THEREOF

(75) Inventors: Thierry Prud'homme, Burgdorf (CH); Catalin Cris, Wunnewil (CH)

(73) Assignee: Roche Diagnostics International AG, Rotkreuz (CH)

( * ) Notice: Subject to any disclaimer, the term of this patent is extended or adjusted under 35 U.S.C. 154(b) by 1325 days.

(21) Appl. No.: 12/272,155

(22) Filed: Nov. 17, 2008

(65) Prior Publication Data

US 2010/0125241 A1    May 20, 2010

(51) Int. Cl.
| | | |
|---|---|---|
| G01N 33/48 | (2006.01) | |
| G01N 31/00 | (2006.01) | |
| G06G 7/48 | (2006.01) | |
| G06G 7/58 | (2006.01) | |

(52) U.S. Cl.
USPC .................... 702/19; 702/22; 703/11; 703/12

(58) Field of Classification Search
None
See application file for complete search history.

(56) References Cited

U.S. PATENT DOCUMENTS

| | | | |
|---|---|---|---|
| 4,398,908 A | 8/1983 | Siposs | |
| 6,368,272 B1 | 4/2002 | Porumbescu | |
| 6,605,072 B2 | 8/2003 | Struys et al. | |
| 6,810,290 B2 | 10/2004 | Lebel et al. | |
| 6,936,029 B2 | 8/2005 | Mann et al. | |
| 7,060,059 B2 | 6/2006 | Keith et al. | |
| 7,109,878 B2 | 9/2006 | Mann et al. | |
| 7,204,823 B2 | 4/2007 | Estes et al. | |
| 7,229,430 B2 | 6/2007 | Hickle et al. | |
| 7,491,187 B2 | 2/2009 | Van Den Berghe et al. | |
| 2003/0032867 A1 | 2/2003 | Crothall et al. | |
| 2003/0055570 A1 | 3/2003 | Ribeiro, Jr. | |
| 2003/0060765 A1 | 3/2003 | Campbell et al. | |
| 2003/0065308 A1 | 4/2003 | Lebel et al. | |
| 2003/0114836 A1 | 6/2003 | Estes et al. | |
| 2003/0212379 A1 | 11/2003 | Bylund et al. | |
| 2004/0122353 A1 | 6/2004 | Shahmirian et al. | |
| 2005/0022274 A1 | 1/2005 | Campbell et al. | |
| 2005/0272640 A1 | 12/2005 | Doyle, III et al. | |
| 2007/0149861 A1 | 6/2007 | Crothall et al. | |
| 2007/0287985 A1 | 12/2007 | Estes et al. | |

FOREIGN PATENT DOCUMENTS

| | | |
|---|---|---|
| WO | 2005061041 A1 | 7/2005 |
| WO | 2005093629 A2 | 10/2005 |
| WO | 2005113036 A1 | 12/2005 |
| WO | 2007016145 A1 | 2/2007 |

OTHER PUBLICATIONS

International Search Report, Aug. 23, 2010 for International Application No. PCT/EP2009/007951, pp. 1-6.

*Primary Examiner* — Larry D Riggs, II
(74) *Attorney, Agent, or Firm* — Dinsmore & Shohl LLP (57) ABSTRACT

A method and system for optimizing post prandial blood glucose excursions for persons with diabetes via computation of time-varying optimal insulin profiles are disclosed. The method builds upon a mathematical model based on the physiologic description of the human glucoregulatory system. Model parameter values are specific for each patient and meal type, and are determined from measured data by minimizing differences between both measurements and model predictions, and which are used to provide the optimal insulin profiles that are useful to diabetics in managing their chronic disease.

20 Claims, 9 Drawing Sheets

PRANDIAL BLOOD GLUCOSE EXCURSION OPTIMIZATION METHOD VIA COMPUTATION OF TIME-VARYING OPTIMAL INSULIN PROFILES AND SYSTEM THEREOF

FIELD OF THE INVENTION

The present invention relates to a method for optimizing post prandial blood glucose excursions for persons with diabetes via computation of time-varying optimal insulin profiles and system thereof.

BACKGROUND OF THE INVENTION

Insulin pumps are thought to improve glucose metabolic control and reduce long-term complications compared to conventional therapy or even compared to multiple daily injections (MDI) therapy. While both continuous subcutaneous insulin infusion (CSII) and MDI fail to reproduce the physiological delivery of insulin exactly, depositing insulin into the subcutaneous tissue instead of the hepatic portal vein, CSII allows one to program changes in basal insulin dosage according to anticipated need and thereby reduce blood glucose variability. This is perhaps the one greatest advantage of CSII. As such, CSII is increasingly used as a means of insulin delivery for those with type 1 diabetes as CSII improves glycaemic control compared to other intensified insulin regimens. CSII makes it possible to better mimic physiological meal related insulin infusion profiles by infusion of time-varying insulin profiles even if this possibility is not exploited by classical methods to control post prandial glucose excursions.

Indeed, with both MDI and CSII, controlling blood glucose excursions after meals is the main challenge for the otherwise more controlled metabolism of a person with diabetes. Classical therapy methods based on insulin administration use a single-shot bolus to correct for the meals. This bolus is calculated on the basis of the meal carbohydrate contents. The dependency of absorption speed on type and size of a meal is not taken into account by the classical therapy method. Therefore differences between "slow" and "fast" absorbing meals are ignored leading to suboptimal control of blood glucose (e.g. and generally speaking, high BG values after meals, e.g. 300 mg/dl, or episodes of hypoglycaemia, are clear indicators of poor control).

Classical therapy methods and systems consider only carbohydrate content and carbohydrate/insulin sensitivity, thereby failing to account for meal composition, size, and absorption speed. This results in inferior control and management of blood glucose. In addition, classical therapy methods and systems consider only customization of insulin dosage, and not the pattern (i.e., dosing amount and timing sequence) of infusion that may provide the best treatment to a diabetic patient. In addition, classical therapy methods only compute meal size dependent single-shot boluses to control post prandial glucose excursions and do not consider time-varying insulin profiles which would provide the best treatment to a person with diabetes.

SUMMARY OF THE INVENTION

It is against the above background that the present provides a number of advantages and features over the prior art, such as for example, providing a method and system thereof which aim to optimize post prandial blood glucose excursions for persons with diabetes via computation of time-varying optimal insulin profiles. According to embodiments of the present invention, which accounts for meal composition and not only meal carbohydrate content, the dosing amount (dosage) and timing sequence of the optimal insulin infusion profile results in a shape or pattern specific to the patient and to the meal by which insulin may be infused in order to reach a predefined postprandial blood glucose profile. The method of the present invention builds upon a dynamical model describing the relationship between infused insulin, meal intake rate and blood glucose concentration. The model parameter values are specific for each patient and meal type, they are determined from measured data and a process which minimizes the differences between measurements and model predictions. This process of determining the model parameters is referred as parameters identification in what follows. The optimal insulin infusion profile for each patient and meal is determined using the model, the determined model parameters for this combination meal/patient, pre-meal measurement, meal size, and insulin infusion history before meal time. This process of computing the optimal insulin profile for a couple patient/meal is referred as optimal insulin profile computation in what follows. The method in one embodiment is implemented in a system such as, for example, comprising a computer desktop tool for a health care provider (HCP) to implement the parameters identification and a handled device for the person with diabetes to implement the insulin profile optimization.

In one embodiment, a method for the computation of an optimal insulin infusion profile useful as a postprandial blood glucose control for a patient/meal combination is disclosed. The method comprises providing a pre-meal measurement of blood glucose concentration; providing size and composition of a meal to be consumed; providing pre-meal insulin infusion history; providing a chosen insulin pattern for the postprandial blood glucose control; and providing a dynamical model having model parameters, which are predetermined for the patient/meal combination. The method also includes computing automatically the optimal insulin infusion profile by minimizing an objective function, which is defined such that if two different insulin profiles are candidates to compensate for a patient/meal combination, the value of the objective function will be lower for the insulin profile which represents the best postprandial blood glucose control for this patient/meal combination and the minimizing resulting in the optimal insulin infusion profile; and providing the optimal insulin infusion profile.

In another embodiment, a system is disclosed which provides an optimal insulin infusion profile useful as a postprandial blood glucose control for a patient/meal combination. The system comprises an input device configured to receive information about a pre-meal measurement of blood glucose concentration, and size and composition of a meal to be consumed; and a memory which contains additional information about a pre-meal insulin infusion history, a chosen insulin pattern for the postprandial blood glucose control, and a dynamical minimal model having model parameters which are predetermined for the patient/meal combination. The system also includes a processor programmed to use the received information and the additional information to compute automatically the optimal insulin infusion profile by minimizing an objective function, wherein the minimizing of the objective function results in the optimal insulin infusion profile; and a display configured to display the optimal insulin infusion profile.

These and other features and advantages of the present invention will further become apparent from the drawings and detailed description provided hereafter.

BRIEF DESCRIPTION OF THE DRAWINGS

The following detailed description of the embodiments of the present invention can be best understood when read in conjunction with the following drawings in which.

DETAILED DESCRIPTION

The following description of the preferred embodiment is merely exemplary in nature and is in no way intended to limit the invention or its application or uses.

Figure 1:
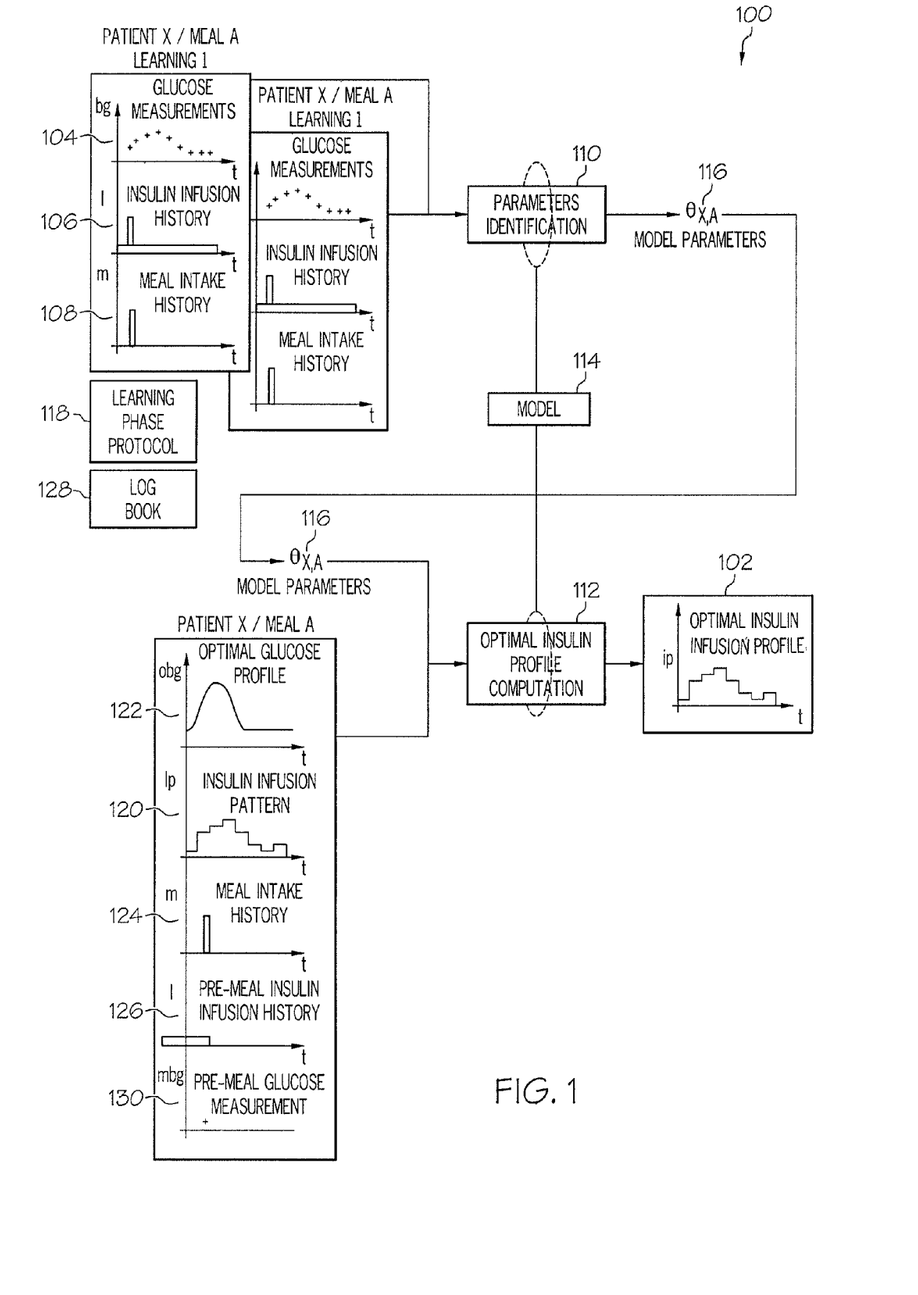
FIG. 1 is a block diagram of an embodiment showing a process according to the present invention which optimize post prandial blood glucose excursions for persons with diabetes via computation of time-varying optimal insulin profiles.

Optimal Insulin Profile Computation for Prandial Blood Glucose Excursion Optimization With reference to FIG. 1, an optimal, prandial insulin infusion computation method, generally indicated by symbol 100, according to one embodiment of the present invention is disclosed. The method 100 helps to compute a time-varying, optimal prandial insulin infusion profile 102 by accounting not only for a patient's pre-meal glucose measurement (i.e., measurements) 130, pre-meal insulin infusion history 126 and meal size and time 124, but also model parameters 116 which are specific to a couple patient/meal. These model parameters for a given couple patient/meal are computed using data collected in the past for the same couple patient/meal. This data collection can be repeated several times (referred as learning 1 to N in FIG. 1) for the same couple patient/meal and contains glucose measurements around the meal 104, insulin infusion history 106 and meal intake history 108. Through use of the present invention, greater control over a patient's blood glucose can be maintained with meal-specific customization of both the insulin dosage and timing sequence (i.e., shape or pattern) of the time-varying, optimal insulin infusion profile 102.

The computation of the optimal insulin infusion profile 102, providing optimal distributed boluses includes two main steps: parameters identification 110 based on a predefined model 114, and insulin profile optimization 112. The predefined model 114 is used to describe the relationship between infused insulin, meal intake, and plasma glucose concentrations. Although the structure of the model 114 is similar for all of the patient/meal combinations, the values of the model parameters 116 differ for every patient/meal combination. These model parameters 116 for every patient/meal combination are computed for a given patient and meal owing to the procedure of the parameters identification 110.

For example, for a given meal, a given patient is asked by its health care provider (HCP) or decides alone to follow a protocol 118. This protocol 118 describes very precisely what kind of measurements should be performed to make sure that the parameters identification 110 will be successful. The implementation of the protocol 118 can take the shape of an electronic reminder which makes sure that the patient does not forget a measurement such as, for example, a series of pre-defined alarms on a blood glucose monitor which when activated reminds the patient to comply with the predefined protocol 118.

In another embodiment, for example, the protocol 118 requests that the patient measures his/her blood glucose concentration two times before the meal, at meal time, and six times after the meal. In other embodiments, the number and timing of measurements may be provided which vary greatly, such as once before the meal, and eight times after the meal over a 24 hour period. Therefore, it is to be appreciated that the predefined protocol 118 is to be used to measure pre-prandial and exactly timed post-prandial situations, to log the associated insulin delivery history, and to analyze basal and bolus needs. Additionally, diary relevant facts like sport, stress, illness, menses, and the size and timing of the meal in question in another embodiment is logged, for example, in an electronic logbook 128 as requested by the protocol 118. In one embodiment, the logbook 128 is used by the HCP to help assess effectiveness of the therapy and relevance of a particular meal as discussed hereafter in a later section.

The predefined protocol 118 is optimized to extract the maximum of information on the status and behavior of the metabolism of the patient out of the additional measurements in combination to an analysis of the available metabolic history from data in the components of the system, e.g. blood glucose meter, diabetes management component, and insulin pump. Accordingly, different protocols may be predefined for this purpose, whereby a proposed protocol in one embodiment may be provided from a diabetes management software component and/or system. In such an embodiment, final selection of the protocol 118 is done by the patient and/or HCP dependant on the seriousness of the meal-related problem, general quality of metabolic control of the patient, and knowledge or estimation of the compliance level of the patient.

Figure 4:
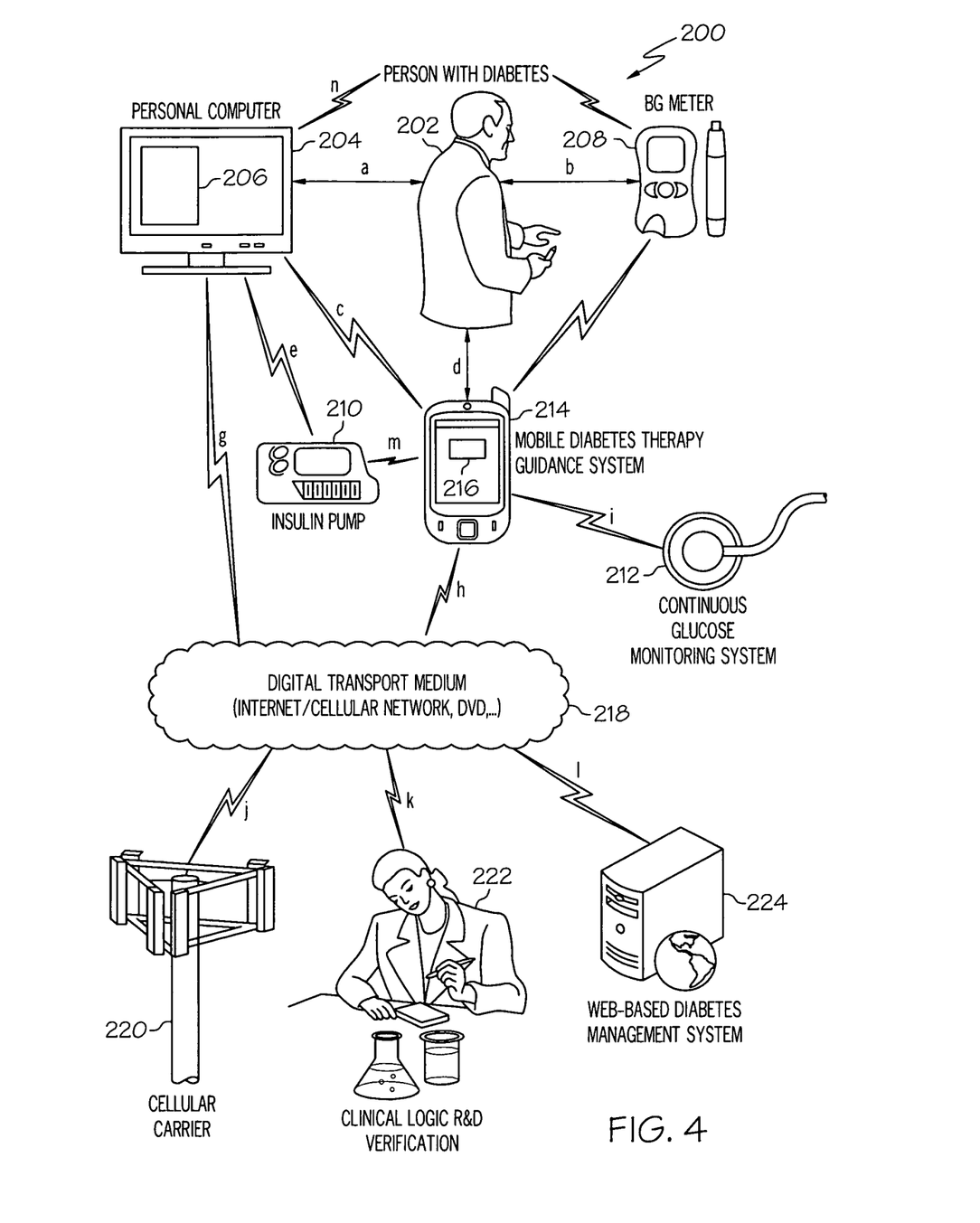
FIG. 4 is a diagram of an embodiment showing a therapy delivery system for optimizing therapy for a diabetic individual according to the present invention.

After the patient has completed the protocol 118 for a given meal, the previously mentioned glucose measurements as well as the profile of infused insulin over a period (e.g., meal time −10 h, meal time +6 h, or other such periods determined by the HCP) and the information regarding the meal (e.g., meal unique identifier, size, composition, absorption rate, amount of carbohydrates, etc.) are saved, for example, in memory of a blood glucose meter 208 and/or a mobile diabetes therapy guidance system 214 (FIG. 4). In another embodiment, additional glucose intakes for compensating low BG values are also included in the previously mentioned information. In still other embodiment, the information (i.e., input data) also includes, but not limited to, blood glucose values coming from spot or continuous measurements performed by the patient during its routine therapy, the insulin infusion history information about meal including, but not limited to, size and composition, and patient demographic data.

The protocol 118 in one embodiment is applied several times for the same meal and/or for different meals between two subsequent visits at the HCP's practice. When visiting the HCP the next time, the HCP will download the saved data and will perform the parameters identification 110 for all meals for which the patient has followed the protocol 118. In this manner, a value set of model parameter 116 is computed for each meal by the parameter identification 110. The structure of the model 114 in one embodiment is a set of ordinary differential equations (linear or nonlinear). In other embodiments, the model 114 may be a model defined by a set of linear or nonlinear partial differential equations, a set of linear or nonlinear ordinary difference equations, a set of linear or nonlinear partial difference equations, a set of linear or nonlinear stochastic ordinary differential equations, a set of linear or nonlinear stochastic partial differential equations, a set of linear or nonlinear stochastic ordinary difference equations, a set of linear or nonlinear stochastic partial difference equations, an autoregressive moving average model, and/or a neural network model. As those skilled in the art understand how to use the above mentioned questions to model the behavior of a complex system, such as diabetes therapy, no further discussion is provided.

The process of parameter identification 110 computes the model parameters 116. For example, one process suitable for parameter identification 110 is the Maximum A Posteriori identification strategy (MAP). In statistics, the method of maximum a posteriori (MAP, or posterior mode) estimation can be used to obtain a point estimate of an unobserved quantity on the basis of empirical data. It is closely related to Fisher's method of maximum likelihood (ML), but employs an augmented optimization objective which incorporates a prior distribution over the quantity one wants to estimate. MAP estimation can therefore be seen as a regularization of ML estimation. See, e.g., Harold W. Sorenson, *Parameter Estimation: Principles and Problems*, Marcel Dekker Inc., 1980. In other embodiments, other methods, which may be used for parameter identification 110, include maximum likelihood estimation, maximum a posteriori estimation with Bayesian priors, least squares fitting, and nonlinear least squares fitting. As parameter identification is well understood by one skilled in the art, no further discussion is provided herein.

Once the model parameters 116 for a coupled patient/meal have been computed, these model parameters 116 together with the structure of the model 114 is used to give a predictor of the glucose metabolism again for the given coupled patient/meal. Accordingly, if a patient has followed the protocol 118 for a given meal, and if the parameters identification 110 for the meal has been performed, then it is possible to predict in advance the glucose excursion for this patient and this meal for any given insulin profile, for any given meal size (the meal should be the same but the size can change) and for any given insulin on board.

Figure 3:
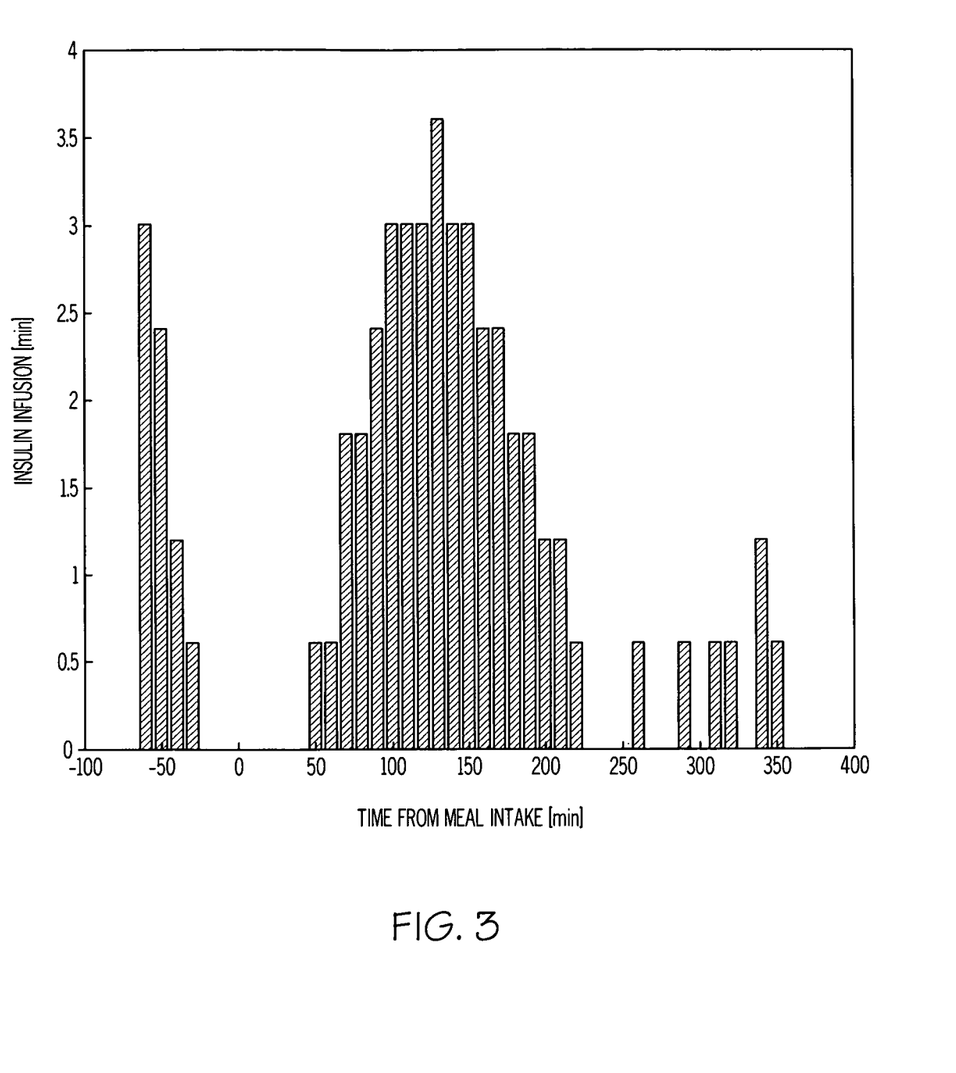
FIG. 3 is a graph illustrating a discretization of an insulin infusion profile.

In one embodiment, the optimal insulin profile computation 112 consists in adjusting the decision variables of the chosen insulin pattern 120 for a particular forecasted meal 124 in order to have a predicted post prandial glucose excursion as close as possible to the chosen post prandial glucose excursion target 112. An objective function is defined to quantify the distance between the predicted post prandial glucose excursion and the target one 112. By this method 100, the value of this objective function is minimized by an optimization algorithm using the profiles 120, 122 and the forecasted meal 124 with the model 114, which results in the calculation of optimal insulin profile 102. For example, this insulin pattern could be a piecewise constant function starting one hour before the meal and ending six hours after the meal. The time period of this piecewise constant function can be 10 minutes as can be seen in FIG. 3. In this case, the decision variable are the 42 (7 hour pattern horizon times 6 periods per hour) levels of the piecewise constant function at each of its intervals.

It is to be appreciated that the calculation of the optimal insulin infusion profile 102 for the corresponding meal is also dependent on the actual meal size, the pre-prandial measured blood glucose value and insulin dose history, and therefore in each instance a new optimization of the insulin infusion profile for the corresponding meal is done. Further factors e.g. sport, stress, conditions like illness or menses will influence the metabolic process and can be taken into account in other embodiments. The calculated optimal insulin infusion profile 102 is then displayed to the patient such as, for example, on device 208 or 214, or computer 204 (FIG. 4), and if accepted, transferred to an insulin pump e.g., insulin pump 210 (FIG. 4), such that insulin is delivered to the patient according to the dosages and timing aspects of the profile 102 as well as documented in a patient record such as provided on computer 204 of the HCP. Further details concerning the model 114 of the present invention is also provided hereafter.

Augmented Minimal Model

The model 114, which may be represented by a number of different types of mathematical equations as mentioned previously above, is derived from an augmentation to a conventionally known minimal model. One suitable overview of the minimal model can be found in Richard N. Bergman and Jennifer C. Lovejoy, editors, *The Minimal Model Approach and Determinants of Glucose Tolerance*, Louisiana State University Press, 1997. As the minimal model is well understood by those skilled in the art no further details beyond what is needed to enable one illustrative embodiment of the augmented minimal model of the present invention is provided.

In the minimal model, an equation may be used to describe the behavior of the insulin action. The input of this equation is the insulin plasma concentration as the minimal model in most cases has in the prior art been used in conjunction with intra venous glucose tolerance tests (IVGTT). Thus, it was originally thought that to the minimal model, an independent sub-model could be added to account for insulin absorption. In such an arrangement, two systems would be serially connected, one for the insulin absorption part and one for the insulin action, whereby the plasma insulin concentration compartment would then be linked between these two sub-systems. However, in such an arrangement the inventors noted that without plasma insulin concentrations measurements, using only the available glucose measurements would not suffice to identify two such independent sub-models. Accordingly, in an embodiment according to the present invention, the two sub-models (insulin absorption and insulin action) are merged resulting in the augmented minimal model 114 according to the present invention. In the augmented minimal model 114 there is no explicit state variable representing the insulin plasma concentration anymore. Instead, in this illustrative embodiment, a linear second order model accounts for both insulin absorption and insulin action parts of the insulin dependent compartment. Still further details of the augmented minimal model 114 are provided hereafter.

Model Inputs

The list of inputs to the augmented minimal model 114 in one embodiment is given as follows: the term $U_{i,sq}$ is the insulin injected subcutaneously in [mU/min]; and the term $U_{cho,mt}$ is normal carbohydrate intakes (meals) in [g/min]. The subscript mt stands for "meal type" such that there are as many inputs as the meal types considered. For purposes of illustration, for example, three meal types mt are considered: Fast, Medium and Slow. There are thus, in this example, three corresponding inputs: $U_{cho,fm}$, $U_{cho,mm}$ and $U_{cho,sm}$, respectively.

Model States Variables

With the above model inputs, there are nine state variables. The state variables are given as follows: the term $Q_{ga}$ is the glucose amount in the accessible compartment [mmol/kg]; the term X is the insulin action [min$^{-1}$]; the term $X_1$ is the first compartment insulin action [min$^{-1}$]; the term $U_{g,gut,fm}$ is the fast carbohydrate intake rate [g/min]; the term $\dot{U}_{g,gut,fm}$ is the fast carbohydrate intake rate time derivative [g/min/min]; the term $U_{g,gut,mm}$ is the medium carbohydrate intake rate [g/min]; the term $\dot{U}_{g,gut,mm}$ is the medium carbohydrate intake rate time derivative [g/min/min]; the term $U_{g,gut,sm}$ is the slow carbohydrate intake rate [g/min]; and the term $\dot{U}_{g,gut;sm}$ is the slow carbohydrate intake rate time derivative [g/min/min]. However, if six of them characterize the three meal types considered and given the fact that only one meal is considered at a time, it can be stated that the model 114 in this illustrative embodiment is of dimension five.

Model Equations

Again, the model 114 can be decomposed into three sub-models: meal absorption, glucose, and insulin absorption/action. The sub-models are described in what follows in the above given order.

Meal Absorption Sub-Model

The two equations describing the meal absorption sub-model are given by the following Equations 1 and 2:

$$dU_{g,gut,mt}/dt = \dot{U}_{g,gut;mt} \qquad (1); \text{ and}$$

$$d\dot{U}g,gut,mt/dt = -2a_{mt}\dot{U}_{g,gut,mt} - a^2_{mt}U_{g,gut,mt} + K_{g,mt}a^2_{mt}U_{cho,mt} \qquad (2),$$

wherein $K_{g,mt}$ is the bioavailability for the meal mt (either fm, mm, or sm for fast, medium and slow meals respectively), and $a_{mt}$ the inverse of the time-of-maximum appearance rate of glucose in the accessible compartment for the considered meal. $U_{cho,mt}$ is the rate of ingested carbohydrates in [g/min]. There are two linear ordinary differential equations for each meal type in the provided illustrative embodiment. Thus, for the three meal types considered, six equations are provided.

Glucose Sub-Model

Equation 3 hereafter describes the behavior of the glucose amount in the accessible compartment, which is given as follows:

$$dQ_{ga}/dt = -XQ_{ga} - S_{g,zero}Q_{ga} + U_{endo} + U_{g,gut}(K_{g\to mmol}/M) \qquad (3).$$

The term on the left-hand side of Equation 3 gives the glucose amount variation in [mmol/kg/min] in the accessible compartment. The first term on the right-hand side deals with the insulin dependent glucose uptake. The transport rate is dependent on the glucose concentration in the accessible compartment $Q_{ga}$ and also on the state variable X representing the insulin action. The term $S_{g,zero}Q_{ga}$ determines the insulin independent glucose uptake, and the term $S_{g,zero}$ is known as the glucose effectiveness at zero insulin. The term $U_{endo}$ determines the insulin independent endogenous production.

The glucose concentration in [mmol/L] Cga is given by Equation 4:

$$Cga = Q_{ga}/V_{ga} \qquad (4),$$

wherein $V_{ga}$ is the accessible volume per body mass.

Insulin Absorption/Action Sub-Model

As already mentioned above in a previous section, the insulin absorption sub-model and the insulin action sub-model have been merged into a single sub-model which is used to account for both. In one embodiment, a Laplace representation of the considered linear model (i.e., insulin subsystem) is represented by Equation 5:

$$X/U_{i,sq} = (K_x/M)/(1+s(1/a_x))^2 \qquad (5),$$

wherein X is the insulin action in [min$^{-1}$], and $U_{i,sq}$ is the insulin infusion rate in [mU/min]. The term $K_x/M$ is the gain of this transfer function and is called the insulin sensitivity in what follows. It must be noticed that it does not correspond to the sensitivity of the original version of the minimal model. The sensitivity in the minimal model defines a relationship between the plasma insulin concentration and the insulin action. This newly defined sensitivity defines a relationship between the insulin action and the subcutaneous insulin infusion rate. The term M is the patient body mass in [kg]. The term $a_x$ is the inverse of the time constant of the insulin absorption/action.

The above Laplace transfer function is equivalent to the two following differential equations:

$$dX/dt = a_x(X_1 - X) \qquad (6); \text{ and}$$

$$dX_1/dt = a_x(K_x(U_{i,sq}/M) - X_1) \qquad (7).$$

In one embodiment, equations 6 and 7 are integrated to determine the initial values for the insulin dependent compartments.

Model Parameters

The model parameters are listed and described in what follows: the term M is the body weight in kilograms [kg]; the term $V_{ga}$ is the volume of the accessible compartment per body mass [L/kg]; the term $K_{g,fm}$ is the bioavailability for fast meals [-]; the term $a_{g,fm}$ is an inverse of time constant for fast meals absorption [min$^{-1}$]; the term $K_{g,mm}$ is the bioavailability for medium meals [-]; the term $a_{g,mm}$ is an inverse of time constant for medium meals absorption [min$^{-1}$]; the term $K_{g,sm}$ is the bioavailability for slow meals [-]; the term $a_{g,sm}$ is an inverse of time constant for slow meals absorption [min$^{-1}$]; the term $K_x$ is an insulin sensitivity [kg/mU]; the term $S_{g,zero}$ is glucose effectiveness at zero insulin [min$^{-1}$]; the term $a_x$ is an inverse of the time constant of the insulin absorption/action [min$^{-1}$]; and the term Uendo is the insulin independent endogenous production [mmol/kg/min]. The terms M and $V_{ga}$ are supposed to be known, the terms $K_{g,mt}$ and $a_{g,mt}$ characterize only the meal absorption part, and remaining parameters are related only to the patient. The next sections describe the optimization method according to embodiments of the present invention.

Preliminary Conditions

In the following example, the parameters of the augmented minimal model 114 are identified for the specific patient/meal combination for which the optimization 112 of the prandial insulin infusion is to be carried out. It is to be appreciated that the parameters in the system implementation embodiment which follows are made available to the software facilitating the optimization performed by the system.

Input Data

The input data needed for the optimization 112 are the following: the infused insulin 106 over a pre-defined time interval before the start of the optimized infusion; at least one pre-meal spot measurement of blood glucose concentration provided in the glucose measurements 104; and at least the size and composition of the meal to be consumed provided in the meal information 108.

Timing

Before the optimization can take place, it is assumed that the patient has inputted the information regarding the meal that he/she plans to eat. If the patient inputs this information some time before the meal intake, the optimization start time can be some time before the meal intake allowing meal insulin to be infused before the meal. It is well known that for fast absorbing meal, meal insulin should be infused before the meal to avoid high glucose values after the meal. Such an anticipation is possible with the current embodiment as soon as the patient inputs the information before the meal. However, if for some practical or safety reasons, the patient does not want meal insulin to be infused before meal time, the optimization start time is simply the meal intake time.

Initial Conditions

To carry out the optimization 112, the states of the model at the optimization start time have to be computed. This process is often referred as initial conditions computation. These initial conditions are derived from the input data as follows: the initial blood glucose value is given by the measured pre-meal value (i.e., pre-meal glucose measurement 130); the initial values for the insulin dependent compartments are computed by integration of the insulin sub-model equations (i.e., Equations 6 and 7) up to the optimization start time point with the pre-meal insulin infusion as input (i.e., infused insulin 126). In addition, all initial values for the meal related compartments are set to zero as it is assumed that the previous meal has been absorbed completely at the intake time of the meal of interest. In other words, the glucose coming from the meal is set to zero at t=0. Accordingly, a meal related carbohydrate intake rate starts at t=0, and the meal related glucose absorption is computed from this rate.

Objective Function

The insulin infusion profile 102, which corresponds to optimal postprandial blood glucose control, is obtained by minimization of the following objective function (Equation 8) with respect to the insulin infusion:

$$F(u(t)) = \int_{t_{start}}^{t_{end}} dt\{[G_M(t, \Theta, u(t)) - G_T(t)]^2\} + \alpha \left\{ \int_{t_{start}}^{t_{end}} dt[u(t) - u_{init}(t)] \right\}^2 \quad (8)$$

The above symbols of equation 8 have the following meaning: $t_{start}$ start time point for optimization (referred as optimization start point in what precedes); $t_{end}$ end time point for optimization; $\theta$ is the set of model parameters; $u(t)$ insulin infusion; $G_M(t, \Theta, u(t))$ blood glucose trace predicted by the model; $G_T(t)$ target blood glucose trace 122; $\alpha$ weight factor; $u_{init}(t)$ insulin amount infused to achieve postprandial blood glucose control during the last level. $t_{start}$ can be 1 hour before the meal for which the patient would like to optimize the prandial glucose excursion. Such a $t_{start}$ allows meal insulin to be infused before the meal intake. $t_{end}$ can be 6 hours after the meal.

Target Blood Glucose Traces

Figure 2:
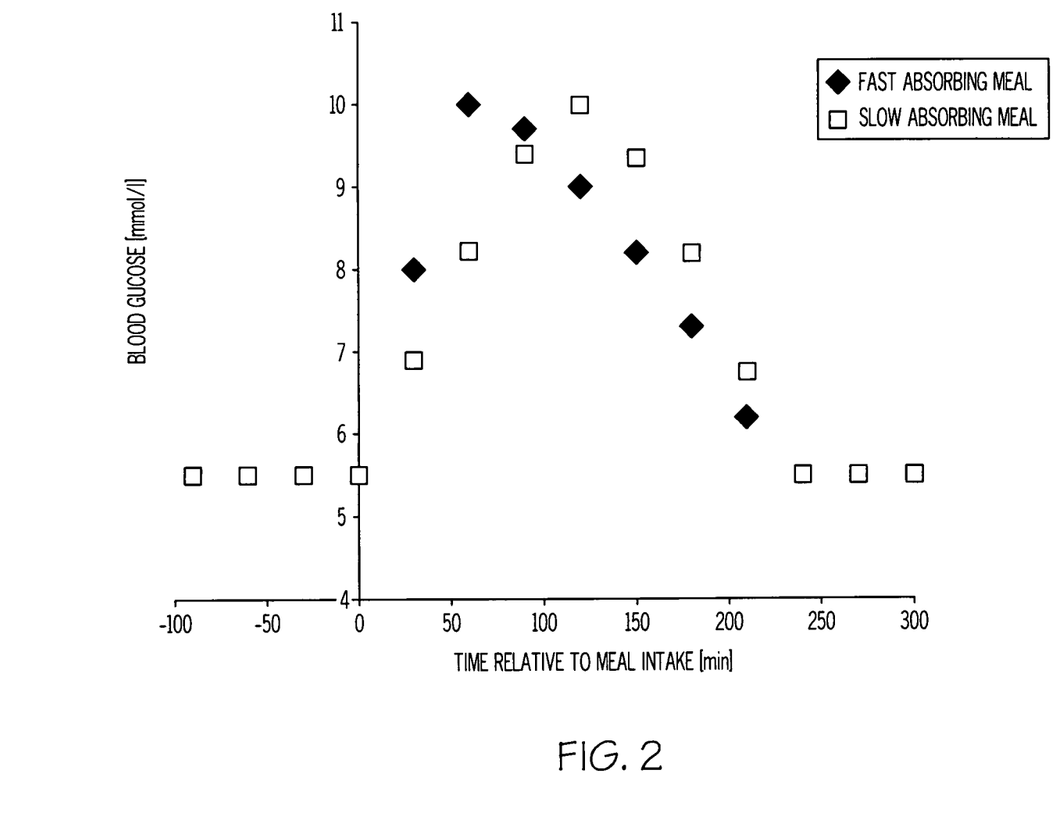
FIG. 2 is a graph of target blood glucose traces for slow and fast meal absorptions.

From a mathematical point of view, it is highly unlikely to optimize such a continuous profile, as the dimension of the problem is infinite. Instead the insulin infusion profile 102 is characterized in one embodiment by a piecewise constant function, whereby each level of the function is a decision variable. Accordingly, the piecewise constant function can be as close as possible to a continuous function as soon as the sampling period of this function is small enough. The target blood glucose profile (i.e., profile 122) mentioned above depends on the meal type. The reason therefore is the fact that, given specific meal absorption characteristics, the same target profile cannot be expected to be targeted for all meals. To account for such differences, two target blood glucose profiles, representing fast and slow absorbing meals for postprandial blood glucose control for type 1 diabetics, are show graphically by FIG. 2. The corresponding numeric values for these target blood glucose profiles are indicated in Table 1.

TABLE 1

Numeric values for the target blood glucose profiles.

| t[min] | BG_fast[mmol/l] | t[min] | BG_slow[mmol/l] |
|---|---|---|---|
| −180 | 5.5 | −180 | 5.5 |
| −150 | 5.5 | −150 | 5.5 |
| −120 | 5.5 | −120 | 5.5 |
| −90 | 5.5 | −90 | 5.5 |
| −60 | 5.5 | −60 | 5.5 |
| −30 | 5.5 | −30 | 5.5 |
| 0 | 5.5 | 0 | 5.5 |
| 30 | 8 | 30 | 6.9 |
| 60 | 10 | 60 | 8.22 |
| 90 | 9.7 | 90 | 9.4 |
| 120 | 9 | 120 | 10 |
| 150 | 8.2 | 150 | 9.35 |
| 180 | 7.3 | 180 | 8.2 |
| 210 | 6.2 | 210 | 6.75 |
| 240 | 5.5 | 240 | 5.5 |
| 270 | 5.5 | 270 | 5.5 |
| 300 | 5.5 | 300 | 5.5 |
| 330 | 5.5 | 330 | 5.5 |
| 360 | 5.5 | 360 | 5.5 |
| 390 | 5.5 | 390 | 5.5 |
| 420 | 5.5 | 420 | 5.5 |

It is to be appreciated that the maximum blood glucose values for fast and slow absorbing meals can be different as well as blood glucose target profiles being multimodal. Therefore, according to another embodiment, the method 100 may be modified such that during an adaptive learning phase, the average blood glucose profile observed while the patient follows the protocol 118 could be used as the departure point for the definition of the target profile.

Insulin Infusion Profile Discretization

A generic insulin infusion profile to be optimized is defined as a discrete profile $u(t_i)$ with the following parameters: resolution, $\Delta t_i = t_i - t_{i-1}$; duration of infusion, $\Delta T = t_{final} - t_{start}$; and anticipation of infusion with respect to meal intake. The anticipation with respect to meal intake is needed due to the discrepancy between the delay in the insulin action and the increase of blood glucose concentration after meal intake. Every element $u_i = u(t_i)$ represents an insulin bolus delivered during the time interval $[t_{i-1}, t_i]$. The amounts of the bolii $u_i$ are varied during the optimization process. FIG. 3 illustrates the discretization of one embodiment of an insulin infusion profile. In this illustrated example, the infusion duration is 420 minutes and there is an anticipation of 1 hour of the insulin infusion with respect to meal intake. The infusion resolution is 10 minutes in the illustrated embodiment, but in other embodiments, other resolutions and durations may be used.

Optimization Method

The problem described by Equation 8 is solved by constrained nonlinear optimizations in one embodiment. The optimization is carried out using the sequential quadratic programming described in the reference entitled *Optimization Toolbox, For Use with Matlab, User's Guide*, Version 2, The MathWorks, Inc., 2000. Constrained nonlinear optimization problems are composed of nonlinear objective functions and may be subject to linear and nonlinear constraints. Active-set sequential quadratic programming (SQP) is used for general nonlinear optimization. Quadratic programming problems involve minimizing a multivariate quadratic function subject to linear equality and inequality constraints. Active set minimizes the objective at each iteration over the active set (a subset of the constraints that are locally active) until it reaches a solution. In other embodiments, other software packages in addition to Matlab, such as for example, NPSOL, NLPQL, OPSYC, and OPTIMA, may also be used to solve the problem described by Equation 8 using SQP. A system embodiment employing the method 100 according to the present invention is now described hereafter. In addition, the objective function may also be minimized in other embodiments using means such as, for example, global optimization, genetic algorithms, simulated annealing, linear programming, stochastic optimization, and calculus of variations. As such minimizing means are well known to those skilled in the art, no further discussion is provided thereon.

FIG. 4 illustrates a system 200 which may be used to implement the method 100 according to the present invention, which computes the insulin infusion profile 102 that is useful in managing treatment of diabetes. Typically, a person with diabetes (PWD) 202 will have multiple devices and software to help with the management of their disease. For example, it is assumed that the PWD 202 or the health care provider (HCP) will have a personal computer 204 running software 206 for tracking health status which includes blood glucose (BG) measurements and insulin dosing, a blood glucose (BG) meter 208 (spot measuring type) for intermittent measurements, an insulin pump 210 for delivering insulin subcutaneously, and optionally a continuous glucose monitoring system 212 for monitoring blood glucose frequently, which may be subcutaneous and/or cutaneous, and/or a mobile diabetes therapy guidance system 214 running therapy guidance software 216, such as implemented on a mobile phone, a personal digital assistance, a notebook computer, and the like. As shown by FIG. 4 and in one embodiment, the PWD 202 (and/or HCP) interacts (arrows a, b, d) with the personal computer 204, the bG meter 208, and optionally, the therapy guidance system 214.

For the purpose of this system example and in other embodiments, the insulin pump 210 and the continuous monitoring system 212 is also used by the PWD 202 and configured through the software 206 of the personal computer 204, therapy guidance software 216 of the therapy guidance system 214, and/or the BG meter 208. For this system example and in other embodiments, devices 204, 208, 210, 212, and 214 contain operating software/firmware that embodies logic to facilitate the PWD 202 to manage his or her diabetes care therapy. It is also to be appreciated that the devices 204, 208, 210, 212, and 214 communicate (arrows e, c, f, and i) with each other in one form or another via wired or wireless data communications (infrared, Blue tooth, RF, etc.) as is known.

In another embodiment of the invention, the therapy guidance system 214 contains logic, for example, embodied in the software 216 which advises the PWD 202 on proper insulin dosing, such as, for example as computed by the method 100 of the present invention. In such an embodiment, the method 100 embodied in the software 216 optimizes the insulin infusion profile 102 (FIG. 1) wherein insulin pump 210 is instructed (arrow m) by the therapy guidance system 214 to infuse insulin according to the profile 102. Additionally, the therapy guidance software 216 in another embodiment offers diary and documentation functions (e.g., via the electronic logbook 128), which can implement and manage a list of supported meals, and which can implement the therapy protocol 118 to ensure compliance and successful results of the method 100.

In still another embodiment, data to and from devices 204, 214 may be provided (arrows g, h) to a web-based diabetes management system 224 via a digital transport medium 218 (arrow l), such as provided in one embodiment as a public network (i.e., the Internet), or via a cellular carrier 220 (arrow J). Such an embodiment is useful in providing updates to and from clinicians and medical health care providers 222 concerning the health condition of the PWD 202, therapy actions and/or recommendations, and/or updates to the software implementing the method 100, such as changes/refinement to the equations used to compute the optimized insulin infusion profile 102. It is to be appreciated that other embodiments of this invention in the environment of FIG. 4 are possible, which is by no means exhaustive. A use case example is now provided hereafter.

Use Case Example

Figure 5:
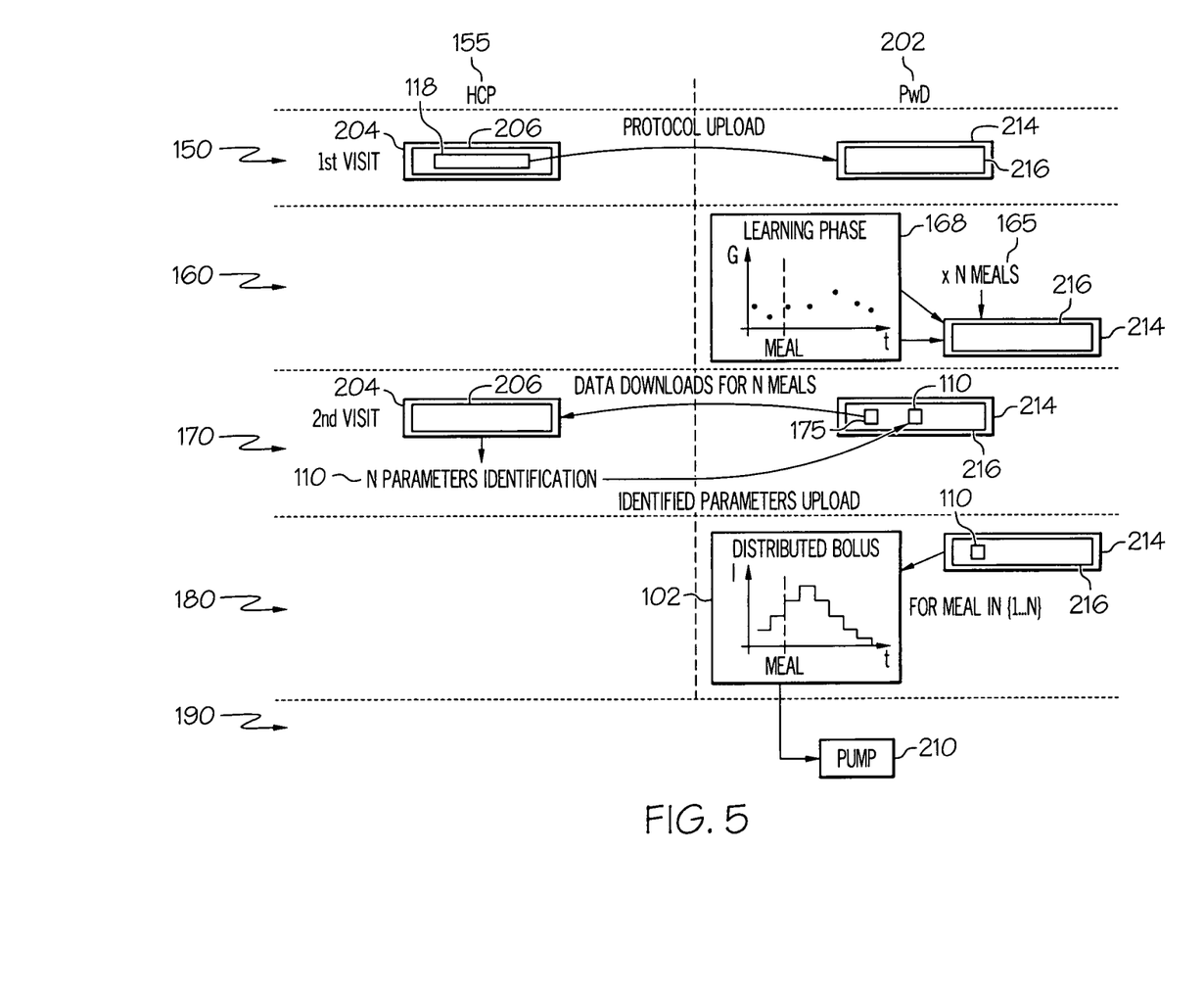
FIG. 5 is a block diagram of a use embodiment illustrating steps to optimize post prandial blood glucose excursions for persons with diabetes via computation of time-varying optimal insulin profiles according to the present invention.

With reference made to FIGS. 1, 4 and 5, a use case example according to an embodiment of the present invention is disclosed. In this use case example, the PWD 202 uses portions of the system 200, which in one embodiment comprises the insulin pump 210, the blood glucose meter 208, and one of the devices 204, 214 implementing the method 100, such as a software application 206, 216, respectively. As illustrated and in one embodiment, data concerning the amount of infused insulin 106 taken over a period of time is provided from the insulin pump 112 to one of the diabetes management devices 204, 214, running software 206, 216 providing the method 100. In this embodiment, reference hereafter is made to device 204, however, it is understood that this example applies equally to device 214. Also as illustrated and in one embodiment, data concerning the glucose measurements 104 taken over a period of time is also provided from the blood glucose meter 208 to device 204.

Data concerning the meal information 110 in one embodiment is inputted directed to the device 204 via an input interface such as a keyboard, stylus, touch screen, touchpad, track ball, voice recognition, etc., or in another embodiment captured via the insulin pump 112 and/or the blood glucose meter 116, or combinations thereof, and then inputted to device 204 and stored thereon in memory as data. Such data is then used by the method 100, implemented on the device 204 as software, to analyze meal dependant absorption speed for the corresponding meal, identify corresponding model parameters 116 of the predefined mathematical model 114 based on current knowledge about human physiology, and calculates an optimized insulin infusion profile 102 for the corresponding meal as detailed previously above. In other embodiments the data may be downloaded to device 204 or device 214, whereby method 100 is performed thereon resulting in the optimized insulin infusion profile 102 being displayed thereon.

With the above described system embodiment, the follow steps are then carried at in this use case example with reference mainly to FIG. 5. In step 150, during a first visit once the above-mentioned tools are available, the PWD 202 together with a health care provider (HCP) 155 identify a list of meals whose control have been noticed to be bad in the last months. The HCP 155 then recommends that the PWD 202 follow a learning phase for one or more times for these identified meals. The HCP 155 then uploads a protocol 118 from the diabetes management software 206 running on the device 204 to the therapy guidance system 214, which is used by the software 216.

Next in step 160, the PWD 202 goes on with life following the protocol 118, and at the appropriate times will indicate to the software 216 of the guidance system 214 that he/she is about to eat a meal 165 which has been previously been identified as problematic. The PWD 202 at this point will apply the classical therapy for this meal but will tell the software 216 to learn about the meal 165 using an adaptive learning phase 168. The software 216 implements a reminder, such as previously described above, that helps the PWD 202 follow the measuring protocol 118. The patient follows the protocol 118 and the measurements together with meal information about history of infused insulin are saved in memory of the device 204 by the software 216. The PWD 202 may repeat the learning phase 168 for the same meal or for any other meals that he/she was told by the HCP that are problematic or also for new meals believed that could be problematic such that a number of data points concerning the meal is available for analysis.

Next in step 170, the PWD 202 again visits the HCP 155. During this second (or latter) visit, the HCP 155 downloads the data 175 saved after all of the learning phases 168 that the PWD 202 has gone through since the last visit. In one embodiment, the data 175 contains information concerning the glucose measurements 104, the infused insulin 106, the meal information 108, and optionally information contained in the logbook 128 (FIG. 1). The HCP 155 then uses the software 206 implementing the method 100 on device 204 to perform the parameters identification 110 for all of the meals concerned. The HCP 155 optionally runs a validation to make sure that the identified parameters 110 will compute reasonable boli, such as in a simulation running on device 204. The identified and optionally validated model parameters 110 are then uploaded to the device 214 for use by the software 216.

Next, in step 180, the PWD 202 goes on with his/her life, and if it happens that he/she is again confronted with a meal for which the PWD 202 has gone through the learning phase 168 in the past, the PWD 202 is now given the opportunity to compute the optimized insulin infusion profile 102 (according to method 100 running on device 214) which provides an optimal distributed bolus for that meal. It is to be appreciated that the PWD 202 still has the freedom to apply the classical therapy. If the PWD 202 decides to have an optimal distributed bolus controlled by the optimized insulin infusion profile 102, then the insulin profile optimization 112 is carried out using the identified model parameters 110 on the device 214.

The computed optimal boli is then displayed on a display to the PWD 202. In one embodiment, the PWD 202 is given the option to modify manually this profile 202 and asks for validation. Once the profile 202 has been accepted, it is then sent to the insulin pump 210 to be infused in step 190. Experimental results obtained with the method 100 are exemplified by the data shown in FIGS. 6 and 7.

Experimental Results

Figure 6A:
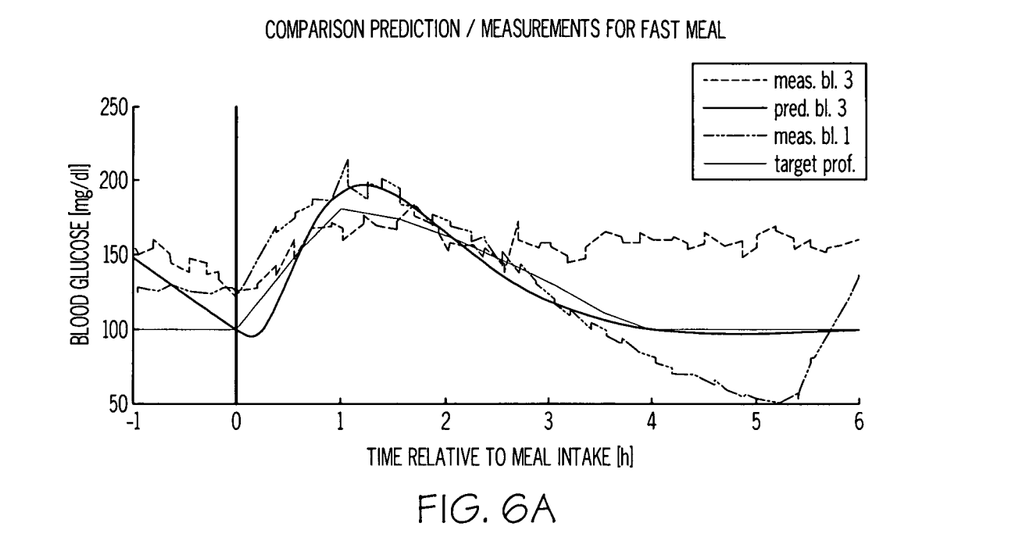
FIG. 6 is a graphical representation of a traditional one-shot bolus compared to distributed bolus therapy according to the present invention for a fast absorbing meal in a clinical trial.
Figure 6B:
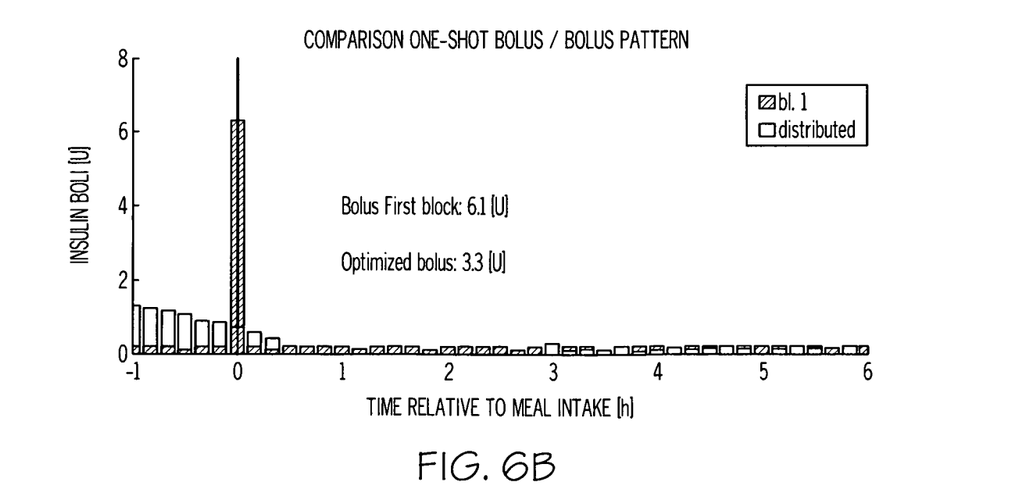

FIG. 6 shows the comparison of glucose traces and insulin infusions obtained with the traditional one-shot bolus versus that obtained when using distributed insulin infusions according to a computed insulin infusion profile 102 in conjunction with the intake of a fast meal. For comparison purposes, the glucose trace predicted by method 100 is shown as well as the targeted glucose profile. When using the optimized insulin distribution it is obvious that no hypoglycemic episode occurs around five hours after meal intake as this was the case when the data used for identification were measured.

Figure 7A:
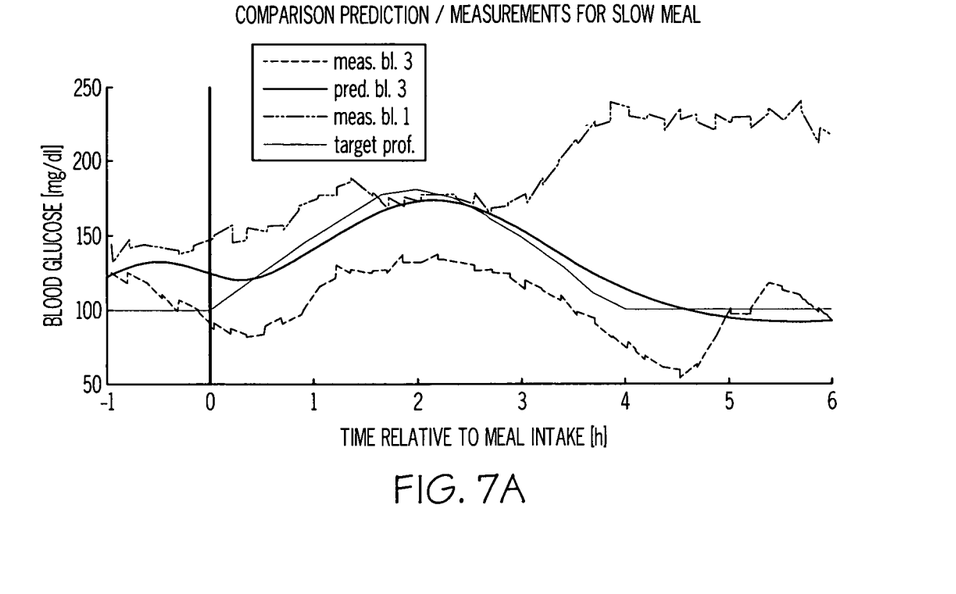
FIG. 7 is a graphical representation of a traditional one-shot bolus compared to distributed bolus therapy according to the present invention for a slow absorbing meal in a clinical trial.
Figure 7B:
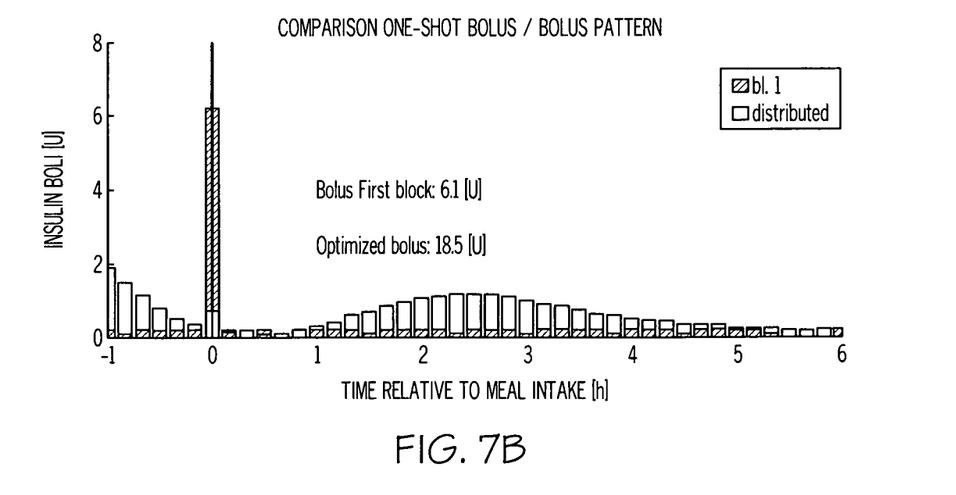

FIG. 7 shows the corresponding data for a slow absorbing meal. The method 100 recommended a more aggressive insulin therapy trying to catch up with the large glucose values, which still show up in the red curve used for the model identification. A hypoglycemic episode occurred at 4.5 h after meal intake in this case. Although the shape of the measured bolus profile 3, obtained when using the optimized insulin distribution, matches the shapes of the predicted and targeted profiles very well it is shifted towards lower glucose values. As for the previous example, the different factors which are currently not taken into consideration by the method 100 as well as the model limitations should explain the observed differences between measurement and prediction. Accordingly, a conservative approach should be adopted in such cases which will minimize the risk for patients by targeting bolus patterns which are dose to current therapy practices.

Figure 8A:
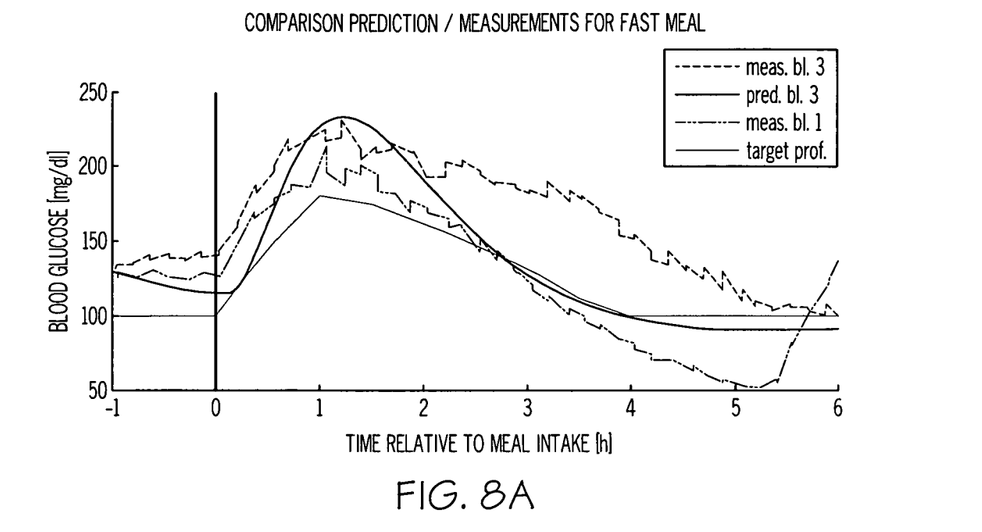
FIG. 8 is a graphical representation of a traditional one-shot bolus therapy compared to an optimized one-shot bolus therapy for a fast absorbing meal according to the present invention in a clinical trial.
Figure 8B:
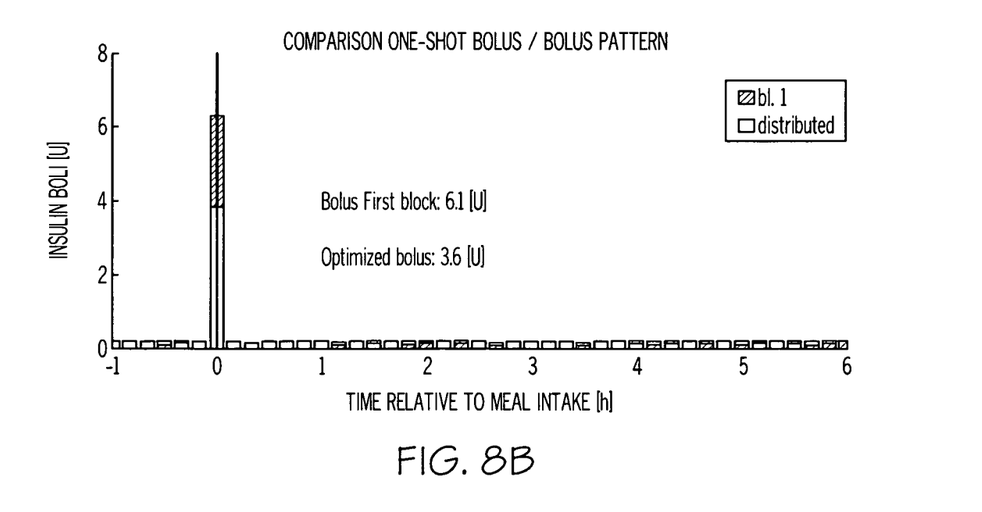
Figure 9A:
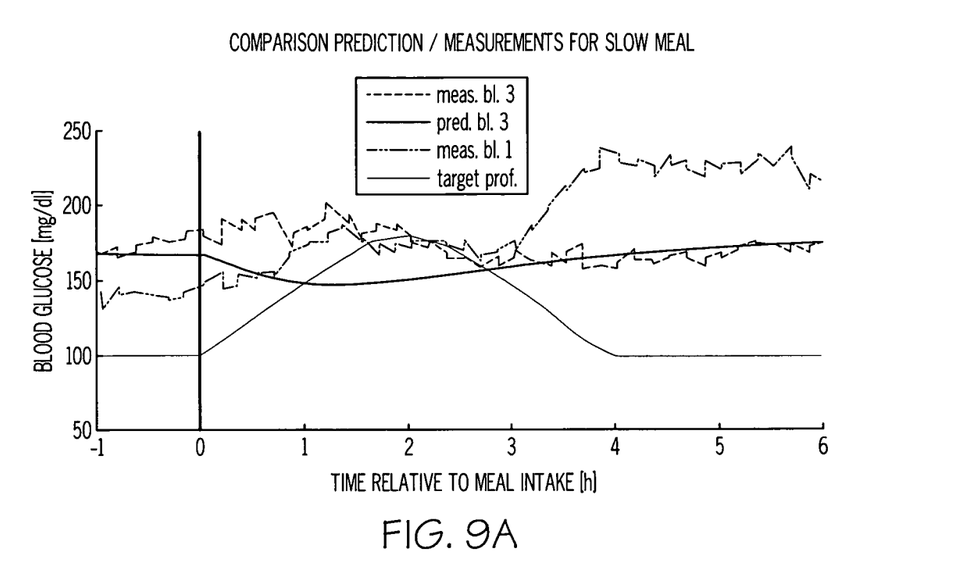
FIG. 9 is a graphical representation of a traditional one-shot bolus compared to optimized one-shot bolus therapy according to the present invention for a slow absorbing meal in a clinical trial.
Figure 9B:
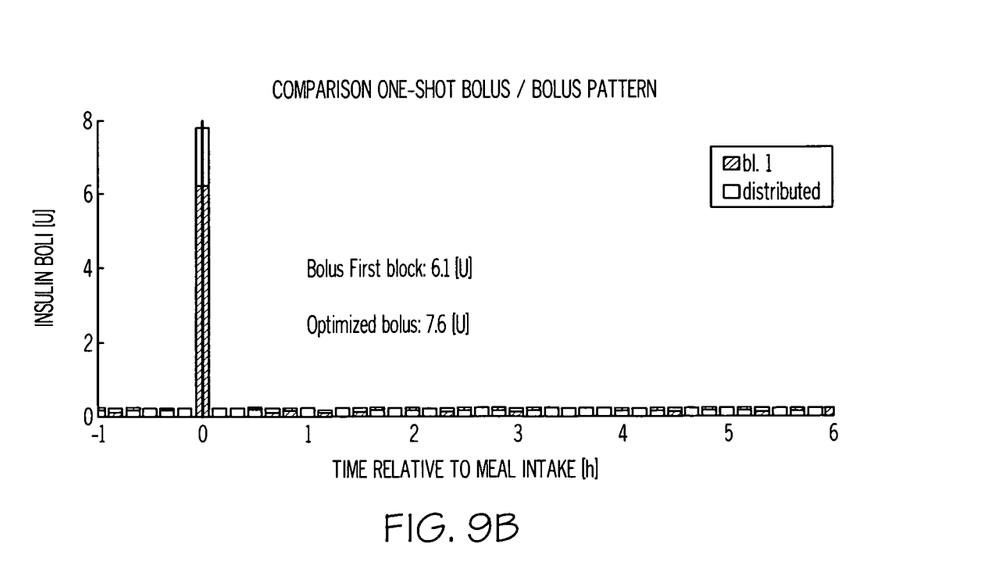

It is to be appreciated that the optimized insulin infusion profile 102 is not restricted to a particular bolus shape. The optimized insulin infusion profile 102 can be of arbitrary shape; in particular, the method 100 can be applied to the optimization of one-shot, dual or multi-wave boluses, too. Examples for applications to the optimization of one-shot boluses are shown in FIGS. 8 and 9. The identification step is not modified by this constraint while the bolus shape has to be constrained to a single bolus during the optimization step. Only the amount of insulin to be infused is optimized in this particular solution.

In another embodiment, the method 100 is generalizes to syringe and pen therapy in a natural way. For such therapy approaches the bolus shape is given by a series of single shot boluses. In order to apply the method, different insulin absorption models for long-acting insulin used for basal needs and short-acting insulin used for meal boluses have to be taken into consideration. Dedicated data are needed for the parameter identification describing the absorption for these particular insulin preparations. Once this has been achieved, the optimization step has to be modified to take into account the particular shape of the insulin infusion. In this embodiment, insulin infusions are restrained to series of pulses whose dosing amounts as well as timing sequence are optimized.

Finally, it is to be appreciated that in terms of activity, insulins are distinguished by their onset, peak, and duration and come in very rapid-acting (e.g., insulin lispro, insulin aspart), rapid-acting (e.g., regular, velosulin), intermediate-acting (e.g., NPH, lente, ultralente), long-acting (e.g., ultralente, insulin glargine), and pre-mixed (e.g., 70/30, 50/50, 75/25) varieties. In order to take into account what insulin is being used, the insulin absorption characteristics are determined from available knowledge and measured data. Once these are known and expressed as corresponding model parameters the method 100 is able to optimize doses and the infusion timing sequences for any such or arbitrary insulin formulations.

Finally, although this application relates to an insulin profile, it is contemplated that the principles disclosed herein may be used for any medication including oral medications in still further embodiments of the present invention.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of operating an electronic device to compute an optimal insulin infusion profile which is used as a postprandial blood glucose control for a specific patient/meal combination, said method comprising:
   providing a pre-meal measurement of blood glucose concentration to the electronic device;
   providing a meal intake comprising size and composition of a meal to be consumed by a patient to the electronic device;
   providing pre-meal history of insulin infusion to the electronic device,
   providing a chosen insulin infusion pattern for the postprandial blood glucose control which defines a target blood glucose trace to the electronic device;
   providing a model having model parameters which are predetermined for the specific patient/meal combination to the electronic device, wherein said model parameters describe a relationship between the infused insulin, the meal intake and the blood glucose concentration of the specific patient/meal combination which values differs from other patient/meal combinations and define a predicted blood glucose trace for specific patient/meal combination;
   computing automatically on the electronic device the optimal insulin infusion profile for the meal intake before an amount of insulin is delivered by optimizing the chosen insulin infusion pattern via minimizing an objective function which defines a relationship between the target blood glucose trace and the predicted blood glucose trace for the specific patient/meal combination, wherein the value of the objective function will be lower for an insulin profile which represents the best postprandial blood glucose control for the specific patient/meal combination, and said minimizing resulting in the optimal insulin infusion profile; and
   providing, via the electronic device, the optimal insulin infusion profile for the meal intake.

2. The method of claim 1, wherein the pre-meal measurement of blood glucose concentration is provided via spot measurements performed during routine therapy.

3. The method of claim 1, wherein the pre-meal measurement of blood glucose concentration is provided via continuous measurements performed during routine therapy.

4. The method of claim 1, further comprises providing information concerning the absorption speed and carbohydrate content of the meal to be consumed.

5. The method of claim 1, further comprises using an insulin pump to provide the pre-meal insulin infusion history.

6. The method of claim 1, further comprises using a blood glucose meter to provide the pre-meal measurement of blood glucose concentration.

7. The method of claim 1, further comprises using a portable electronic device to record data concerning the pre-meal insulin infusion history, the pre-meal measurement of blood glucose concentration, and the size and composition of a meal to be consumed, and providing the recorded data concerning the pre-meal insulin infusion history, the pre-meal measurement of blood glucose concentration, and the size and composition of a meal to be consumed to the electronic device.

8. The method of claim 1, wherein the model is selected from the group of models consisting of a set of linear or nonlinear ordinary differential equations, a set of linear or nonlinear partial differential equations, a set of linear or nonlinear ordinary difference equations, a set of linear or nonlinear partial difference equations, a set of linear or nonlinear stochastic ordinary differential equations, a set of linear or nonlinear stochastic partial differential equations, a set of linear or nonlinear stochastic ordinary difference equations, a set of linear or nonlinear stochastic partial difference equations, an autoregressive moving average model, and a neural network model.

9. The method of claim 1 wherein a meal related glucose absorption is computed from a meal related carbohydrate intake rate for use in the objective function.

10. The method of claim 1, further comprises performing parameter identification to predetermine the model parameters.

11. The method of claim 10, wherein the parameter identification is a parameter identification method selected from the group consisting of maximum likelihood estimation, maximum a posteriori estimation, maximum a posteriori estimation with Bayesian priors, least squares fitting, and nonlinear least squares fitting.

12. The method of claim 1, wherein the objective function is minimized using means selected from the group consisting of global optimization, genetic algorithms, simulated annealing, linear programming, stochastic optimization, and calculus of variations.

13. The method of claim 1, wherein the objective function is defined by:

$$F(u(t)) = \int_{t_{sstart}}^{t_{end}} dt\{[G_M(t, \Theta, u(t)) - G_T(t)]^2\} + \alpha \left\{ \int_{t_{start}}^{t_{end}} dt[u(t) - u_{init}(t)] \right\}^2$$

where $t_{start}$ is a start time point for optimization, $t_{end}$ is an end time point for optimization, $u(t)$ is an insulin infusion amount according to the chosen insulin infusion pattern, $G_M(t, \Theta, u(t))$ is the predicted blood glucose trace predicted by the model, $G_T(t)$ is the target blood glucose trace, $\alpha$ is a weight factor, and $u_{init}(t)$ is an insulin amount infused to achieve the postprandial blood glucose control for the patient//meal combination.

14. The method of claim 10, wherein said electronic device is selected from the group consisting of a desktop computer, and a portable electronic device providing a diabetes therapy guidance system.

15. The method of claim 1, wherein the optimal insulin infusion profile is provided to an insulin pump of the patient.

16. The method of claim 1, further comprises modifying insulin dosage and timing sequence of insulin infusion according to the optimal insulin infusion profile when the patient indicates at a subsequent time that the meal is to be consumed.

17. The method of claim 16, wherein the modifying is carried out automatically on an insulin pump of the patient.

18. The method of claim 1, wherein the optimal insulin infusion profile is provided to a display of the electronic device, and said method further comprises permitting acceptance of the displayed optimal insulin profile before use as the postprandial blood glucose control for the patient/meal combination.

19. A system which provides an optimal insulin infusion profile useful as a postprandial blood glucose control for a specific patient/meal combination, said system comprising:

an input device configured to receive information about a pre-meal measurement of blood glucose concentration, and a meal intake comprising size and composition of a meal to be consumed;

a memory which contains additional information about a pre-meal history of insulin infusion, a chosen insulin infusion pattern for the postprandial blood glucose control which defines a target blood glucose trace, and a dynamical minimal model having model parameters which are predetermined for the patient/meal combination and describe a relationship between the infused insulin, the meal intake and the blood glucose concentration of the specific patient/meal combination which values differs from other patient/meal combinations and define a predicted blood glucose trace for specific patient/meal combination;

a processor programmed to use the received information and the additional information to compute automatically the optimal insulin infusion profile for the meal intake before an amount of insulin is delivered by optimizing the chosen insulin infusion pattern via minimizing an objective function which defines a relationship between the target blood glucose trace and the predicted blood glucose trace for the specific patient/meal combination, wherein the value of the objective function will be lower for an insulin profile which represents the best postprandial blood glucose control for the specific patient/meal combination, and wherein said minimizing of the objective function results in the optimal insulin infusion profile; and a display configured to display the optimal insulin infusion profile.

20. The method of claim 1, wherein the insulin infusion profile is a piecewise constant function.

* * * * *

UNITED STATES PATENT AND TRADEMARK OFFICE
CERTIFICATE OF CORRECTION

PATENT NO. : 8,527,208 B2
APPLICATION NO. : 12/272155
DATED : September 3, 2013
INVENTOR(S) : Thierry Prud'homme et al.

It is certified that error appears in the above-identified patent and that said Letters Patent is hereby corrected as shown below:

In the Specification

Col. 1, Line 45, "hypoglycaemia" should read --hypoglycemia--;

Col. 1, Line 63, "that the present provides" should read --that the present invention provides--;

Col. 12, Lines 56-57, "the follow steps are then carried at in" should read
      --the following steps are then carried out in--;

Col. 14, Line 12, "which are dose to" should read --which are close to--; and

Col. 24, Line 24, "the method 100 is generalizes to" should read --the method 100 is generalized to--.

Signed and Sealed this
First Day of July, 2014

Michelle K. Lee
*Deputy Director of the United States Patent and Trademark Office*